US010743978B2

(12) United States Patent
Olivera et al.

(10) Patent No.: US 10,743,978 B2
(45) Date of Patent: Aug. 18, 2020

(54) DEVICES AND SYSTEMS FOR LUNG TREATMENT

(71) Applicant: PulmonX Corporation, Redwood City, CA (US)

(72) Inventors: Ryan Olivera, Granite Bay, CA (US); Srikanth Radhakrishnan, Cupertino, CA (US)

(73) Assignee: Pulmonx Corporation, Redwood City, CA (US)

( * ) Notice: Subject to any disclaimer, the term of this patent is extended or adjusted under 35 U.S.C. 154(b) by 686 days.

(21) Appl. No.: 15/430,080

(22) Filed: Feb. 10, 2017

(65) Prior Publication Data
US 2017/0151052 A1   Jun. 1, 2017

Related U.S. Application Data

(62) Division of application No. 13/174,565, filed on Jun. 30, 2011, now Pat. No. 9,592,008.
(Continued)

(51) Int. Cl.
*A61B 5/00* (2006.01)
*A61F 2/04* (2013.01)
(Continued)

(52) U.S. Cl.
CPC ............... *A61F 2/04* (2013.01); *A61B 1/018* (2013.01); *A61B 1/2676* (2013.01);
(Continued)

(58) Field of Classification Search
CPC ... A61B 5/1076; A61B 5/6852; A61B 1/1018; A61B 1/2676; A61F 2/04
(Continued)

(56) References Cited

U.S. PATENT DOCUMENTS 4,362,167 A   12/1982   Nicolai et al.
5,010,892 A    4/1991   Colvin et al.
(Continued)

OTHER PUBLICATIONS

Notice of Allowance dated Nov. 3, 2016 for U.S. Appl. No. 13/174,565.
(Continued)

*Primary Examiner* — Max F Hindenburg
(74) *Attorney, Agent, or Firm* — Wilson Sonsini Goodrich & Rosati

(57) ABSTRACT

Devices, systems, and methods for measuring the diameter of an airway in a human or animal subject are disclosed. The device comprises a flexible catheter body having a proximal end and a distal end. Flexible sizing elements are disposed along and extend approximately orthogonally from the catheter body. The sizing elements have different heights from one another and are configured to fit through the working channel of a bronchoscope. Devices, systems, and methods for redirecting airflow through a lung airway are also disclosed. The method comprises introducing into the airway a catheter comprising a distal end, a proximal end and an elongated portion therebetween, wherein the distal end comprises an airway closing mechanism, and wherein the proximal end comprises an actuator to actuate the airway closing mechanism; and actuating the airway closing mechanism to at least partially close the airway.

8 Claims, 5 Drawing Sheets

Related U.S. Application Data

(60) Provisional application No. 61/360,809, filed on Jul. 1, 2010.

(51) Int. Cl.
*A61B 5/107* (2006.01)
*A61B 1/018* (2006.01)
*A61B 1/267* (2006.01)
*A61B 17/12* (2006.01)
*A61B 90/00* (2016.01)
*A61B 17/00* (2006.01)
*A61M 25/00* (2006.01)

(52) U.S. Cl.
CPC .......... *A61B 5/1076* (2013.01); *A61B 5/6852* (2013.01); *A61B 17/12104* (2013.01); *A61B 2017/0034* (2013.01); *A61B 2090/061* (2016.02); *A61F 2002/043* (2013.01); *A61M 2025/0008* (2013.01)

(58) Field of Classification Search
USPC ....................................................... 600/587
See application file for complete search history.

(56) References Cited

U.S. PATENT DOCUMENTS

| | | | |
|---|---|---|---|
| 5,919,147 A | 7/1999 | Jain | |
| 6,019,739 A * | 2/2000 | Rhee | A61F 2/2496 33/512 |
| 6,287,290 B1 | 9/2001 | Perkins et al. | |
| 6,450,976 B2 | 9/2002 | Korotko et al. | |
| 6,682,520 B2 | 1/2004 | Ingenito | |
| 6,709,401 B2 | 3/2004 | Soltesz et al. | |
| 6,878,141 B1 | 4/2005 | Perkins et al. | |
| 6,997,189 B2 | 2/2006 | Biggs et al. | |
| 7,144,392 B2 | 12/2006 | Kaji et al. | |
| 7,186,259 B2 | 3/2007 | Perkins et al. | |
| 7,717,115 B2 | 5/2010 | Barrett et al. | |
| 7,814,912 B2 * | 10/2010 | George | A61B 17/12022 128/200.24 |
| 8,012,106 B2 | 9/2011 | Mangiardi et al. | |
| 8,136,526 B2 | 3/2012 | Perkins et al. | |
| 8,728,013 B2 * | 5/2014 | Perle | A61B 5/1076 600/591 |
| 9,592,008 B2 | 3/2017 | Olivera et al. | |
| 2003/0051733 A1 | 3/2003 | Kotmel et al. | |
| 2003/0228344 A1 | 12/2003 | Fields et al. | |
| 2005/0010138 A1 | 1/2005 | Mangiardi et al. | |
| 2005/0016530 A1 | 1/2005 | McCutcheon et al. | |
| 2005/0061322 A1 | 3/2005 | Freitag | |
| 2006/0064039 A1 | 3/2006 | Griego et al. | |
| 2006/0130830 A1 | 6/2006 | Barry | |
| 2006/0162731 A1 | 7/2006 | Wondka et al. | |
| 2006/0264772 A1 | 11/2006 | Aljuri et al. | |
| 2006/0276807 A1 | 12/2006 | Keast et al. | |
| 2007/0005083 A1 | 1/2007 | Sabanathan et al. | |
| 2007/0043350 A1 | 2/2007 | Soltesz et al. | |
| 2007/0203396 A1 * | 8/2007 | McCutcheon | A61B 1/00082 600/173 |
| 2007/0221230 A1 | 9/2007 | Thompson et al. | |
| 2007/0225747 A1 | 9/2007 | Perkins et al. | |
| 2008/0200797 A1 | 8/2008 | Kotmel et al. | |
| 2011/0220104 A1 | 9/2011 | Wondka et al. | |

OTHER PUBLICATIONS

Office Action dated Feb. 26, 2014 for U.S. Appl. No. 13/174,565.
Office Action dated Apr. 5, 2016 for U.S. Appl. No. 13/174,565.
Office Action dated Apr. 6, 2015 for U.S. Appl. No. 13/174,565.
Office Action dated Jul. 18, 2013 for U.S. Appl. No. 13/174,565.
Office Action dated Sep. 9, 2014 for U.S. Appl. No. 13/174,565.

* cited by examiner

DEVICES AND SYSTEMS FOR LUNG TREATMENT

CROSS-REFERENCE TO RELATED APPLICATIONS

This application is a divisional of U.S. patent application Ser. No. 13/174,565, filed Jun. 30, 2011 (now U.S. Pat. No. 9,592,008), which claims priority under 35 U.S.C. § 119(e) to U.S. Provisional Patent Application Ser. No. 61/360,809, entitled Devices and Systems for Lung Treatment, filed Jul. 1, 2010, the full disclosures of which are hereby incorporated by reference.

BACKGROUND OF THE INVENTION

1. Field of the Invention

This invention relates generally to devices and methods for treating lung disease.

2. Description of the Related Art

Lung diseases are a problem affecting several millions of people. Chronic obstructive pulmonary disease (COPD), for example, is a significant medical problem affecting 16 million people or about 6% of the U.S. population. Lung cancer, as another example, is among the most prevalent forms of cancer, and causes more than 150,000 deaths per year.

One of the prevalent forms of treating COPD is the use of lung volume reduction (LVR) techniques. One of the emerging methods of LVR involves the endoscopic introduction of prostheses or implants into pulmonary passageways. Such a method and prosthesis is described, for example, in U.S. patent application Ser. No. 11/682,986. The prosthesis will typically restrict air flow in the inhalation direction, causing the adjoining lung compartment to collapse over time. The prosthesis, also called an endobronchial valve (EBV), is intended to control airflow into a lung compartment and may consist of a one-way, silicone, duckbill valve attached to a metallic self-expanding retainer that is covered with a polymer membrane. The EBV is implanted in the target airway using a delivery catheter inserted through the working channel of a bronchoscope. Upon implantation, the EBV allows distal air to vent from the isolated lung compartment (typically a lobe or segment) during exhalation but does not allow refilling of this compartment during inhalation. With each respiratory cycle, the amount of air in the target lung compartment is reduced (pneumoreduction), allowing better functioning lung compartments to take over more of the work of breathing. This method has been suggested as an effective approach for treating lung compartments that are not subject to collateral ventilation.

To ensure a good fit of an EBV and to prevent EBV migration from the original location in the airway where it is implanted, it is necessary to select an appropriately sized EBV for the target airway. Therefore, it is imperative to place the EBV implant in an airway that has a diameter within the EBV size range and that has is long enough to accommodate the EBV. Catheter-based devices for vascular measurements are unsuitable or too complex for measuring lung passageway diameters for EBV implantation. U.S. Pat. No. 6,450,976, for example, discloses a device to be used as an attachment to a catheter for measuring length as well as vascular diameter. The device uses rotation of an outer barrel relative to an inner tubular member to effect measurement. Measurement is provided by radially movable elements that contact the vascular wall. U.S. Pat. No. 5,919,147 discloses a similar catheter-based device that uses radially moving arms that expand out of the end of a tube to measure the diameter of a vessel. Measurement is made via graduations located axially at the proximal end of the catheter. Contact between the radial arms and the vessel must be detected by the surgeon in both the above devices. One drawback of these devices is their complex construction and operation. Since each requires rotation in order to effectuate measurement, they require two handed operation. In addition, their suitability for use with a bronchoscope for the specific case of airway diameter measurement is not established.

Therefore, a need exists for a quick and convenient method and device for determining whether an airway is suitable for placement of an EBV or other implant for effective LVR and/or for selecting an appropriately sized EBV or other implant for use in a given airway. Ideally, such a method/device could be used to either approximate a diameter and/or length of a potential target airway or could be used to confirm or select a size of EBV that is appropriate for a given airway. At least some of these objectives will be met by the embodiments described herein.

In certain situations, for example when an airway is too big or too small for EBV placement, another method to assist the lung volume reduction may be desirable. Indeed, several existing methods exist for endobronchial lung volume reduction (ELVR), with and without the use of restriction devices. U.S. Patent Publication No. 2005/0061322, for example, discloses a method in which the airway is sealed after air in the lung compartment is aspirated using an occlusion catheter. U.S. Pat. No. 6,997,189 discloses a method of contracting the diseased lung tissue using anchoring elements attached to cords, which are pulled through a catheter. U.S. Patent Publication No. 2007/0221230 discloses an implant that is used to bend a portion of the airway to effect lung volume reduction. Other methods of treatment have been disclosed that involve completely sealing the airway. These include use of plug-forming substances such as swellable collagen or metal as disclosed in U.S. Pat. Nos. 6,287,290, 6,878,141, 6,709,401 and 7,186,259. Installation of plug devices or obturators is disclosed in U.S. Pat. No. 7,144,392 and U.S. Patent Publication No. 2007/005083. Further methods of sealing lung passageways include inducement of fibrosis in the bronchial tubes by introducing an irritant substance such as disclosed in U.S. Pat. No. 6,682,520, U.S. Patent Publication Nos. 2006/0130830 and 2006/0276807.

Despite the innovations in endoscopic lung volume reduction, further improvements and alternative methods and systems would still be desirable. The embodiments described herein seek to achieve at least some of the objectives described above.

SUMMARY OF THE INVENTION

The present application discloses devices and methods for assessing the diameter of an airway to select a size of a pulmonary implant for placing in the airway and/or for confirming that a size of implant selected will work in that airway. The devices and methods may also be used to actually measure or approximate a diameter of the airway.

In one aspect of the present invention, an airway sizing device may include a flexible catheter body having a proximal end and a distal end. First and second flexible sizing elements are disposed along and extend approximately orthogonally from the catheter body. The sizing elements have different heights from one another and are configured to fit through the working channel of a bronchoscope. In one embodiment, the first sizing element has a first height corresponding to a maximum diameter of a prosthesis to be implanted in the airway, and the second sizing element has a second height corresponding to a minimum diameter of the prosthesis.

The first sizing element may include two flexible tabs disposed approximately opposite one another across the catheter body, and the second sizing element may include two flexible tabs disposed approximately opposite one another across the catheter body. From the tip of one tab across the catheter body to the tip of the opposite tab may be referred to as a "height" of a sizing element. In one embodiment, the sizing elements are disposed proximally along the catheter body relative to the distal end, and a distance between the distal end and the sizing elements corresponds to a length of the prosthesis to be implanted in the airway.

In another aspect of the present invention, a method for selecting a size of a pulmonary implant to be implanted an airway in a human or animal subject may include: inserting a bronchoscope into the airway; advancing an elongate airway measuring device through a channel in the bronchoscope to expose within the airway a distal end of the measuring device and first and second flexible sizing elements disposed near the distal end and extending approximately orthogonally relative to a longitudinal axis of the measuring device, where the sizing elements have different heights from one another; observing, using the bronchoscope, the flexible sizing elements in relation to a wall forming the airway; and selecting the size of the pulmonary implant based on the observation of the sizing elements.

In one embodiment, the observing step comprises observing whether the sizing elements touch a wall of the airway. In another embodiment, the observing step comprises observing the flexible sizing elements in relation to the distal end of the catheter.

In another aspect of the present invention, a method of redirecting airflow through a lung airway may involve: introducing into the airway a catheter having a proximal end, a distal end, and an airway closing mechanism at or near the distal end, wherein the airway closing mechanism is selected from the group consisting of a stapler, a suture applier, a clip applier, an energy delivery device and a chemical delivery device; and using an actuator at or near the proximal end of the catheter to activate the airway closing mechanism to at least partially close the airway. The airway may be completely or partially closed. The method may further include choosing the airway from among multiple airways based on a determination of the presence of collateral ventilation. In various embodiments, the closing mechanism may involve stapling, suturing, clipping, ablating, cryogenically treating, applying other forms of energy, or the like.

In some embodiments, the method may further include activating a lung compartment collapsing mechanism to collapse a lung compartment connected to the airway. In various embodiments, the collapsing mechanism may include a staple, a clip applier, a chemical sealant, a one-way flow element, a suturing string, a suction tube, an ablation device, a cryogenic treatment device, another form of energy delivery device, or the like. The method may also include activating a lung compartment collapsing mechanism to collapse a lung compartment connected to the airway. In various embodiments, the collapsing mechanism may be a staple, a clip applier, a chemical sealant, a one-way flow element, a suturing string, a suction tube, an ablation device, a cryogenic treatment device, another form of energy delivery device, or the like.

Further aspects and embodiments of the present invention are set forth herein.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE PREFERRED EMBODIMENT

Although the detailed description contains many specifics, these should not be construed as limiting the scope of the invention but merely as illustrating different examples and aspects of the invention. Various modifications, changes and variations may be made in the disclosed embodiments without departing from the spirit and scope of the invention.

Airway Sizing Device. In one embodiment, an airway (or "bronchial") sizing device includes a catheter with sizing elements, as described further below. The sizing device is used for assessing one or more sites within a lung ("airways" or "air passageways") to determine whether they are suitable for implantation of an implant, such as an endobronchial valve (EBV) and/or to select a size of EBV or other implant for a target airway. The bronchial sizing catheter facilitates accurate placement of a correctly sized implant (or "prosthesis") to facilitate a suitable fit within the passageway and reduce chances of migration of the prosthesis. Prior to implantation of the prosthesis, the sizing catheter is typically introduced into an airway via a viewing scope such as a bronchoscope. The sizing catheter comprises sizing elements and/or a depth marker, which are viewable via the viewing scope. The sizing elements and/or the depth marker are viewed via the viewing scope to determine if the airway is suitable for a prosthesis of a given size. Thereafter, the prosthesis is implanted in the target airway, typically using a flexible delivery catheter that is guided to the target airway by inserting it through the working channel of a bronchoscope.

Figure 1A:
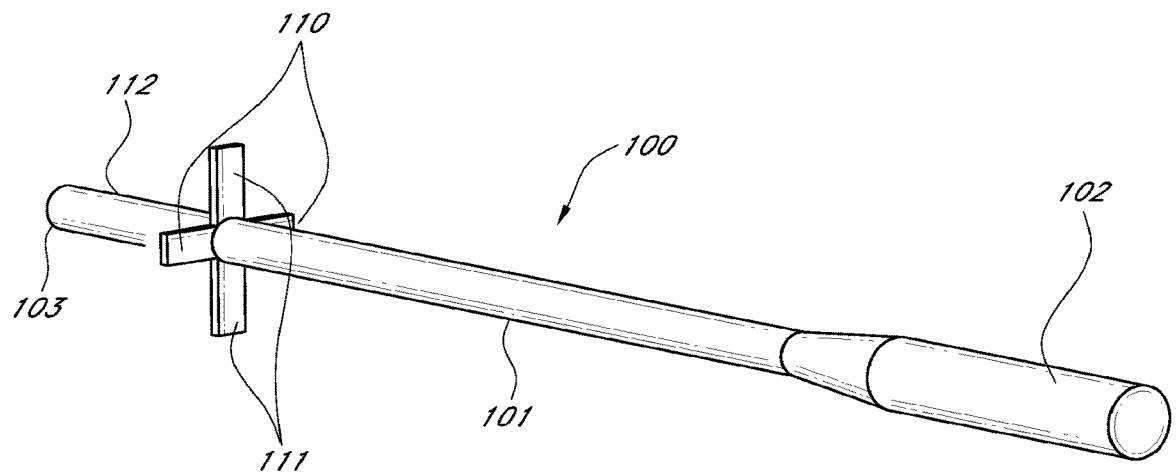
FIG. 1A shows a bronchial sizing catheter according to one embodiment.

Referring to FIG. 1A, one embodiment of an airway sizing device 100 includes a catheter body 101 having a proximal end 102 and a distal end 103. The proximal end 102 may optionally include a handle (not shown). A small sizing element 110 and a large sizing element 111 are disposed along the catheter body 101, closer to the distal end 103 than the proximal end 102. The sizing elements 110, 111 help a user assess/approximate a diameter of a target airway to help select a size for an EBV or other implant to be placed in the airway. The sizing elements are shown in this embodiment near distal end 103, but in alternative embodiments they may be disposed at any suitable location along the catheter body 101. In this embodiment, the sizing elements 110, 111 are flexible tabs that extend radially outward from the longitudinal axis of the catheter body 101. Flexibility allows the tabs to collapse along the side of the catheter body 101 during advancement of the sizing device 100 through a working channel of a bronchoscope or other delivery device.

In the embodiment shown, the catheter body 101 includes a distal portion 112 that extends between the sizing elements 110, 111 and the distal end 103. In this embodiment, the distal portion 112 is approximately as long as an EBV (or other implant in alternative embodiments) to be implanted in an airway. Thus, the distal portion 112 may be used as a depth gauge, as will be described further below.

Figure 1B:
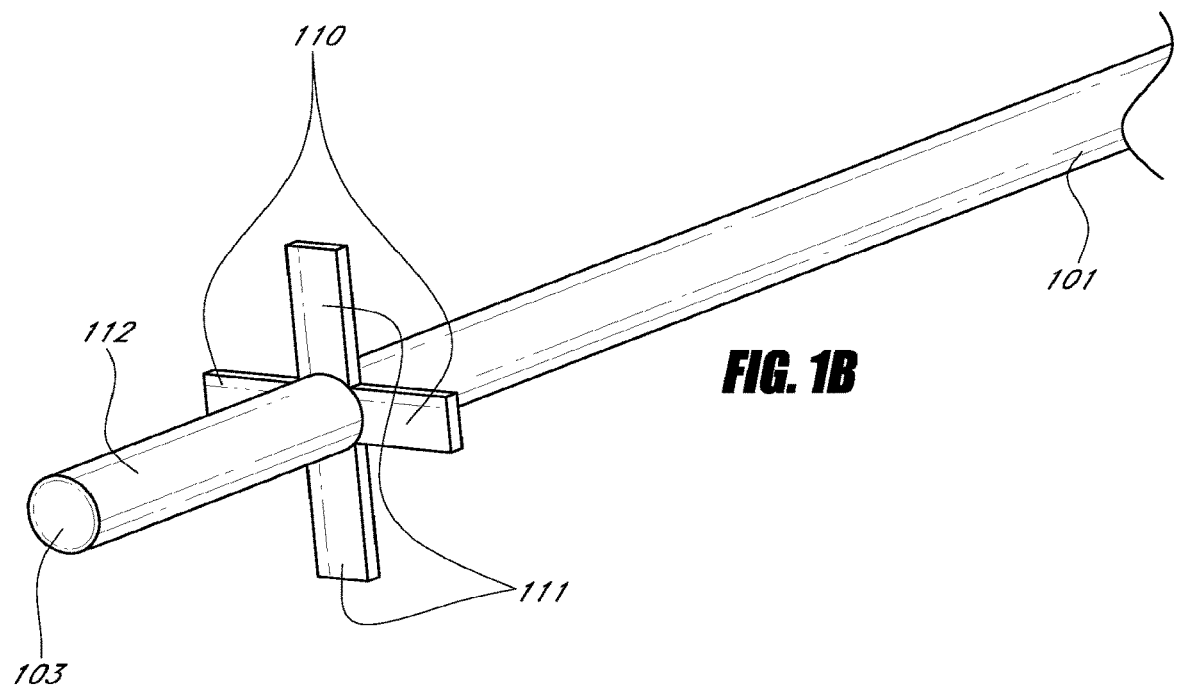
FIG. 1B shows a detailed view of the measuring elements of the bronchial sizing catheter.

Referring now to FIG. 1B, the sizing elements 110 and 111 and the depth marker 112 are shown in greater detail. In the embodiment shown, the sizing elements comprise two sets of radially extending tabs 110 and 111. The tabs making up the small sizing element 110 are set 180 degrees apart from each other, so that the small sizing element 110 can be said to have a "height" measured from the tip of one tab across the catheter body 101 to the tip of the opposite tab. (Although the word "height" is used herein to describe a measurement of a sizing element from a tip of one tab to a tip of another tab disposed across the catheter body 101, the term "length" could be easily substituted for the term "height.") In one embodiment, the height of the small sizing element 110 may correspond to a minimum diameter that an EBV or other implant must have to fit within a given airway. Similarly, the tabs making up the large sizing elements 111 are set 180 degrees apart from each other and have another, larger height measured from tip to tip. This larger height may correspond to a maximum diameter of an EBV or other implant that may be implanted in a given airway. The sizing elements 110, 111 are made of any flexible polymer so that they can fit through a working channel of a bronchoscope and then unfurl to assume their full heights once they are free of the working channel and exposed in a lung passageway. The material of the sizing elements is also intended to be sufficiently soft and flexible so as to not cause trauma to the lung tissue during introduction, measurement and removal. Optionally, the sizing elements may be of a different color than the rest of the catheter body to facilitate viewing via the viewing scope.

Some types of pulmonary implants, such as some EBVs, expand upon deployment. For example, some EBVs are essentially Nitinol, expandable stents, covered with a polymer and including a polymeric valve attached to the inner wall of the stent body. The EBV is typically housed in a delivery device in a compressed or collapsed state, and when it is emitted from the delivery device it expands to a deployed configuration and diameter. In this deployed configuration, the EBV exerts a pressure against an airway wall, which holds it in place within the airway. Typically, an EBV of this type may be suitable for use airways having a range of diameters, due to its ability to expand. For example, one size of EBV may fit in airways having diameters between about 3 mm and about 5 mm, and another size of EBV may fit in airways having diameters between about 4 mm and about 6 mm. Generally, therefore, the sizing device 100 described herein is used to assess whether and EBV in its expanded/deployed configuration will fit appropriately within an airway. Of course, there are other types of pulmonary implants, and the sizing device 100 in various embodiments may be used in conjunction with a number of such implants. Generally, the sizing device 100 will assess airway size to determine whether a given implant will work in its deployed state in that airway.

In various embodiments, the sizing elements 110, 111 may have any of a number of suitable "heights." For example, the small sizing element 110 may range in height from between about 2 mm to about 6 mm and ideally from between about 3 mm to about 5 mm. The larger sizing element may range in height from between about 3 mm to about 8 mm and ideally between about 4 mm and about 6 mm. Additionally, in various embodiments, the sizing device 100 may include more than two sizing elements. For example, for more detailed airway diameter approximations, three or more sizing elements may be included. Also, in some embodiments a kit may be provided with multiple sizing devices 100, with each sizing device 100 having differently sized sizing elements. For example, if there are two sizes (diameters) of EBV available for use in a patient, two different sizing devices 100 may be provided in a kit. A user may view a potential target airway using a bronchoscope, may estimate which size of EBV would be ideal for that airway, and then may use the sizing device 100 that corresponds to that EBV diameter to confirm that it will be the best EBV size for that airway. If the user's first estimate is incorrect, he/she may use the second sizing device 100 to confirm that the other size of EBV would actually be better. This is only one example, of course, and in various embodiments any number and combination of sizes of sizing elements 100 may be provided.

In addition to assessing the diameter of a target airway, the sizing catheter 100 may also be used to determine whether the airway is long enough for implantation of an EBV or other pulmonary implant. If the airway shorter than the length of an EBV, for example, the EBV might not implant firmly within the airway upon deployment and thus might more easily be coughed out or "migrate" (move to another location in the airways/lungs). In the embodiment shown in FIGS. 1A and 1B, the length of the distal portion 112 is approximately as long as the length of an EBV to be implanted in the airway (or other implant in alternative embodiments). In use, the physician may advance the sizing device 100 until the extreme distal end 103 contacts a branching section at the end of the target airway. If the sizing elements 110, 111 are located within the airway when the distal end 103 abuts the branch, then the airway is long enough to accept the EBV or other implant. If the sizing elements 110, 111 are outside of (proximal to the proximal end of) the airway, then the airway may be too short for implanting the EBV or other implant. Thus, as mentioned above, the distal portion 112 of the catheter body 101 may be used as a depth gauge to determine that a sufficient deployment zone exists for placement of a prosthesis at the desired location in the lung passageway. Optionally, the distal portion 112 may be of a different color than the rest of the catheter body 101, such as a color that contrasts with the color of airway tissue, to facilitate viewing through the bronchoscope.

In an alternative embodiment (not shown), the sizing elements 110, 111 may be positioned at a different location along the catheter body 101, for example farther distal than those shown in FIGS. 1A and 1B. Such an embodiment may not include a distal portion 112 that acts as a depth gauge but may instead include a depth marker on the catheter body 101 that is visible through a bronchoscope and that is positioned proximal to the distal end 103 by a length that corresponds to a length of an EBV or other pulmonary implant to be implanted in the airway.

Figure 2:
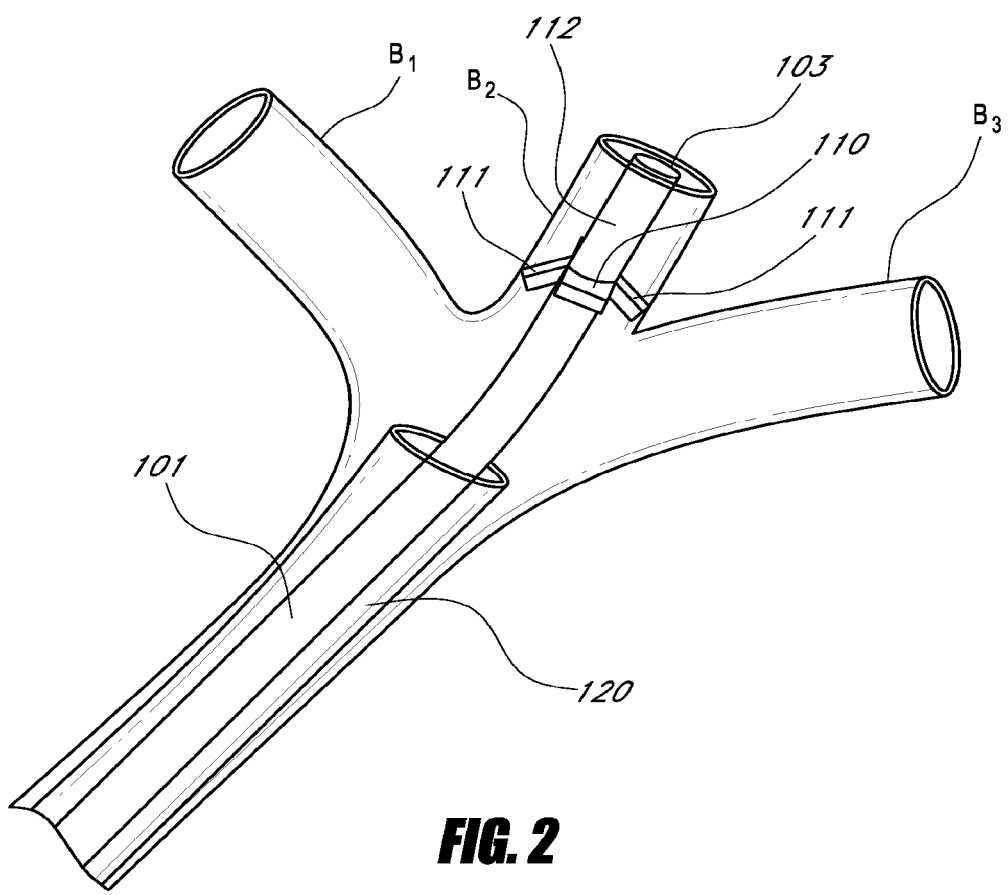
FIG. 2 shows the bronchial sizing catheter in use inside a passageway of a lung.

With reference now to FIG. 2, in use, the sizing catheter 100 is typically introduced through the working channel of a bronchoscope 120 to expose the sizing elements 110, 111 within the target airway $B_2$. The sizing elements 110, 111 and the distal portion 112 may then be used to assess the size of the target airway $B_2$ and its suitability for a given EBV or other pulmonary implant. Or, in other words, the size of the airway may be assessed to select an appropriate size of pulmonary implant to be used. This is shown in greater detail in FIG. 2, where the sizing catheter 100 is shown inserted through the working channel of the bronchoscope 120, which has been guided into a target passageway. The sizing elements 110, 111 are sized to tell a user that a particular EBV or other implant, in its deployed state, will fit within that airway. Typically, in the embodiment shown, if the tips on the tabs of the smaller sizing element 110 are touching the airway wall, the EBV or implant size that has been selected is too big (i.e., has too large of a deployed diameter) for that airway. If, on the other hand, the tips of the smaller sizing element 110 are not touching the airway wall but the tips of the larger sizing element tabs 111 are touching the wall, then the EBV or other implant size that has been selected is suitable for that airway. If the larger sizing element tips 111 are not touching the wall, then the EBV or implant has a diameter that is too small for that airway. In this way, a user can quickly assess an airway diameter relative to a selected implant size and either confirm that the implant size is correct, select a different implant size, use a different sizing device to confirm that a different implant size will work, or decide not to insert an implant at all in that airway.

In any embodiments, the user may use the airway sizing device 100 not just to select a size of an EBV or other pulmonary implant or confirm that a selected size is suitable but also to actually measure or approximate a diameter of the target airway. For example, if the smaller sizing element 110 has a height of 4 mm and its tips just barely touch a wall of an airway, the user may approximate that the airway is about 4 mm in diameter.

In the example shown in FIG. 2, the bronchoscope 120 is placed in a bronchus with three sub-branches $B_1$, $B_2$ and $B_3$ stemming therefrom. As an example, $B_2$ has been chosen as the target passageway. To assess suitability of $B_2$ for placement of an implant, the distal end 103 of the catheter 100 is introduced into the ostium (or further) of $B_2$ via the bronchoscope and thereafter observed. As shown in FIG. 2, the larger sizing element tabs 111 have contacted the airway walls and are shown bent, whereas the smaller sizing element tabs 110 do not contact the passageway wall, and are unbent. Such an observation indicates that the diameter of the target passageway is between the maximum and minimum limits of the EBV or other pulmonary implant that has been selected for implantation. Thus, $B_2$ would be determined to be suitable for implantation of the prosthesis. In contrast, if the smaller sizing element 110 were bent against the passageway wall, it would show that the selected prosthesis was too big for the passageway. Similarly, if neither the smaller element 110 nor the larger element 111 touched the passageway wall, it would show that the selected prosthesis was too small for the passageway.

As also evident in FIG. 2, the sizing elements 110, 111 are within the target airway, so the length of the airway is sufficient to accept an implant. (The distal branching against which the distal end 103 of the sizing device 100 is abutting is not visible in FIG. 2.) Therefore, in the example shown in FIG. 2, the airway $B_2$ appears to be suitable for implanting a prosthesis of the size calibrated to the catheter. This observation can be easily made by direct visualization through the bronchoscope 120.

Optionally, the sizing device 100 may be configured to carry and deploy one or more prostheses at the site being measured. Alternatively, the sizing device 100 may be configured just for sizing and may be withdrawn prior to introduction of a delivery catheter configured to carry and deploy a prosthesis.

The above embodiment was illustrated using two sets of sizing elements 110, 111 that are axially placed 90 degrees apart from each other. Alternatively, in other embodiments, any other angle convenient for bronchoscopic measurement can be used. Alternatively, additional sets of elements can be used on additional axes to represent more size compatibilities, for example, if prostheses of different sizes are to be implanted within the same lung segment.

Figure 3:
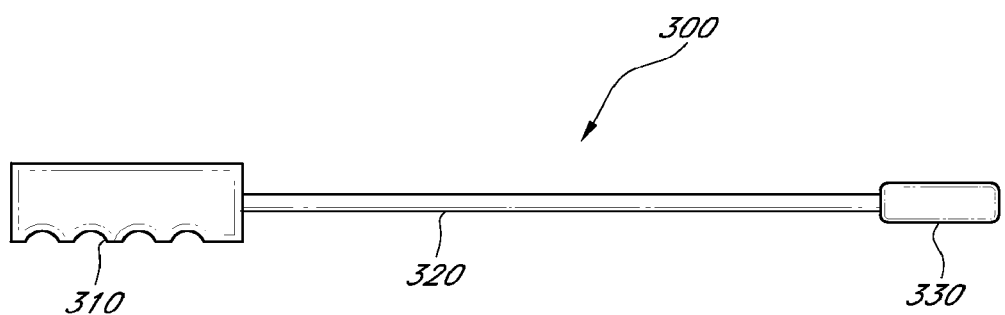
FIG. 3 is a diagram showing an airway closing device in accordance with one embodiment.

Airway Suturing Device. With reference now to FIG. 3, in another embodiment, an endoscopic airway closing device 300 may include an actuator 310 disposed at or near the proximal end of the device 300, an airway closing mechanism 330 disposed at or near the distal end of the device 300, and a delivery shaft 320, between the proximal and distal ends of the device 300. Actuator 310 comprises controls for activating the airway closing mechanism 330. Delivery shaft 320 houses internal mechanisms that communicate actuation from actuator 310 to closing mechanism 330. The airway closing mechanism 330 may be any mechanism or implement suitable for closing the airway, such as a suture or staple. Optionally, a lung compartment collapsing mechanism (not shown) could be provided at the distal end in addition to the airway closing mechanism 330. Such a lung compartment collapsing mechanism may include but is not limited to a suture, staple, vacuum suction, or the like. The actuator for this mechanism would also be located at the proximal end of the device. Optionally, prior to use of the closing device 300, a suitable location for airway closing may be determined by measuring collateral ventilation as disclosed in co pending U.S. Patent Publication Nos. 2003/0051733, 2006/0264772 and 2008/0200797, all of which are incorporated herein by reference.

Figure 4A:
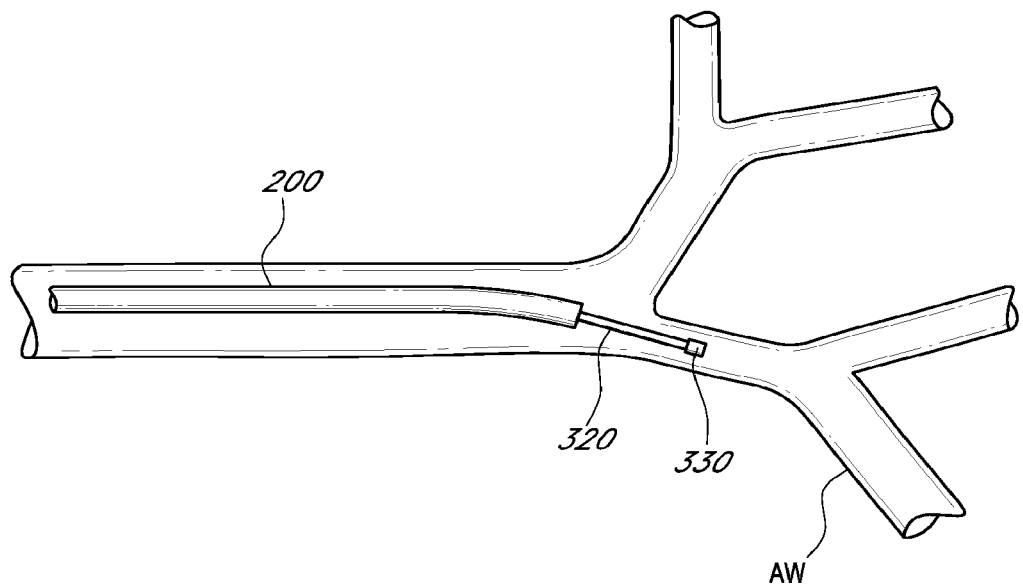
FIG. 4A is a diagram showing the introduction of the airway closing device into a target airway.
Figure 4B:
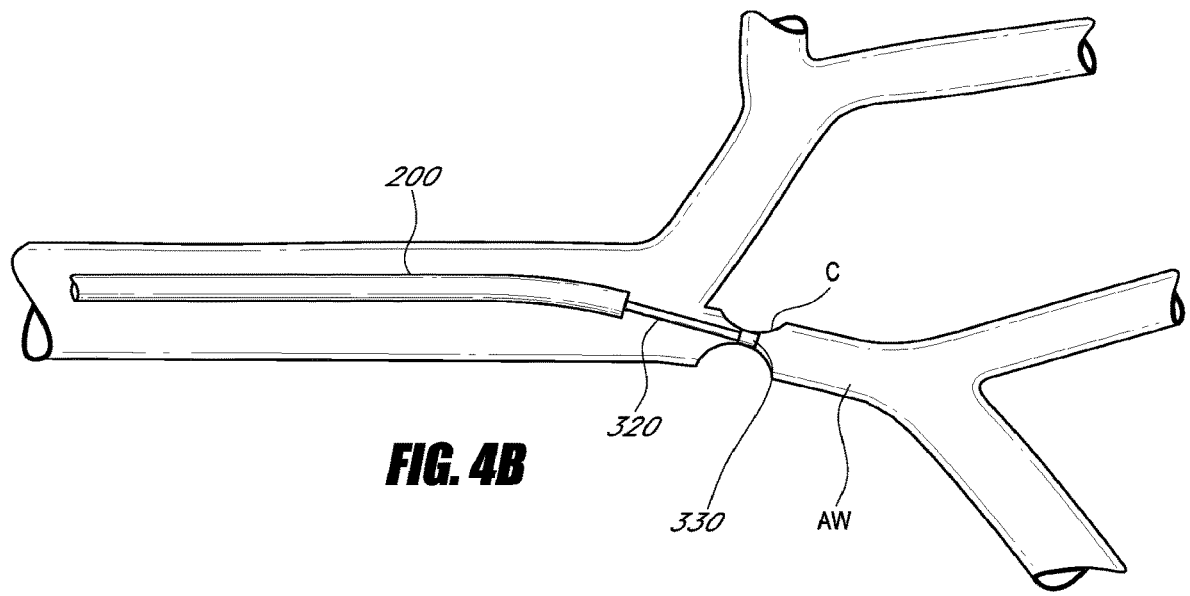
FIG. 4B is a diagram showing the closing of the target airway.
Figure 4C:
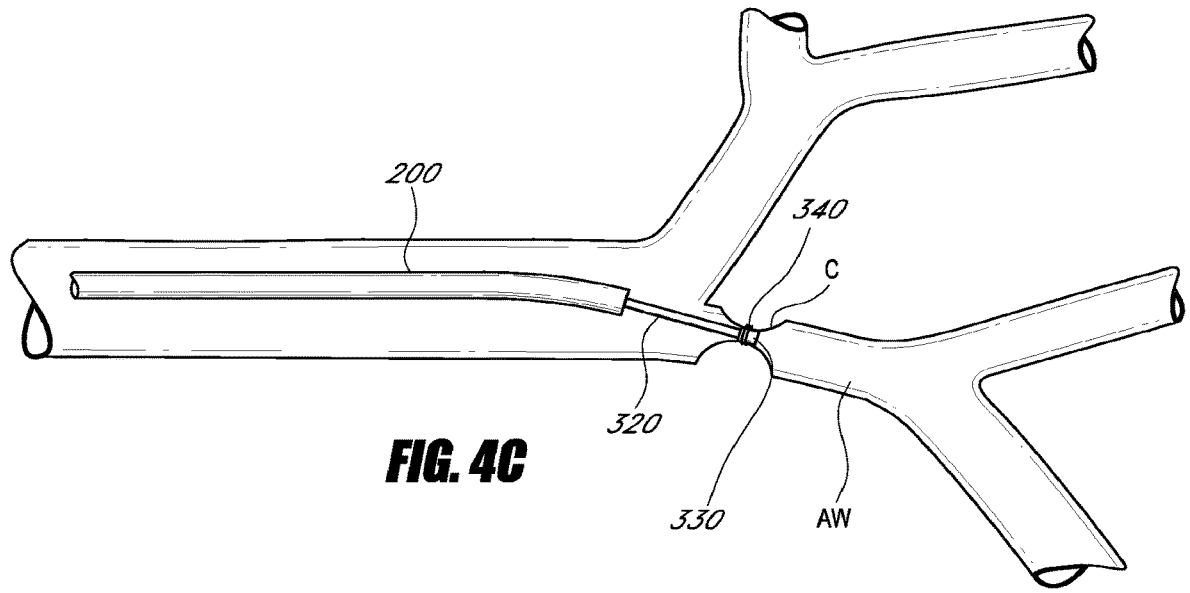
FIG. 4C shows the suturing of the target airway.

Referring now to FIGS. 4A-4E, a method for delivering the airway closing mechanism 330 is shown. As shown in FIG. 4A, once a location is chosen, the endoscopic airway closing device 300 may be delivered to the target airway through a bronchoscope 200, such that the airway closing mechanism 330 is delivered to the desired airway closing point. Thereafter, as shown in FIG. 4B, the airway closing mechanism 330 is activated to close the target airway. The airway closing mechanism 330 produces a constriction C. In this embodiment, as shown in FIG. 4C, a suture 340 (or alternatively any other suitable closing implement) is deployed from the airway closing mechanism 330 to constrict the air passageway. In various embodiments, an airway may be closed using any suitable closure means, such as but not limited to stapling, suturing, clipping, ablating and/or cryogenically treating.

Figure 4D:
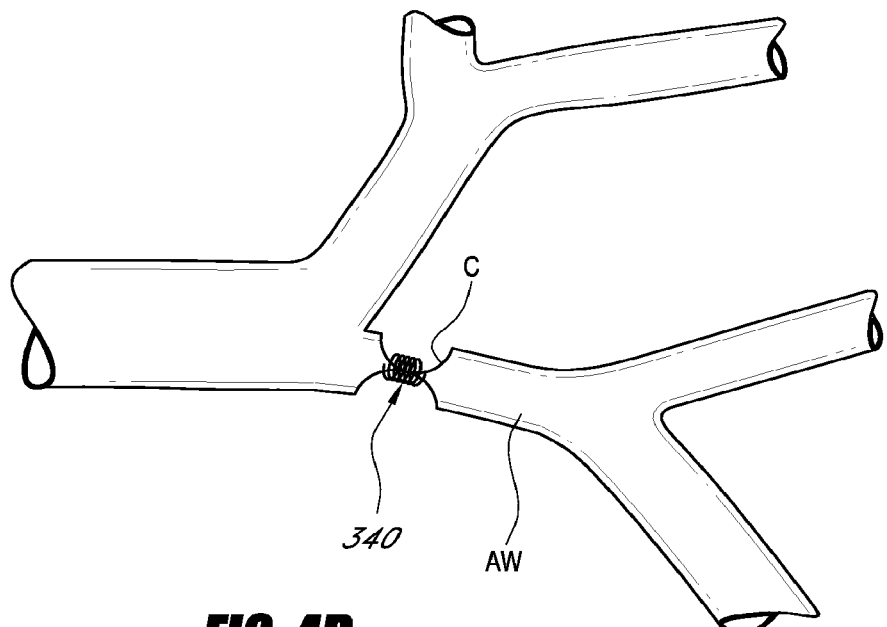
FIGS. 4D and 4E show full and partial closing of the target airway respectively.
Figure 4E:
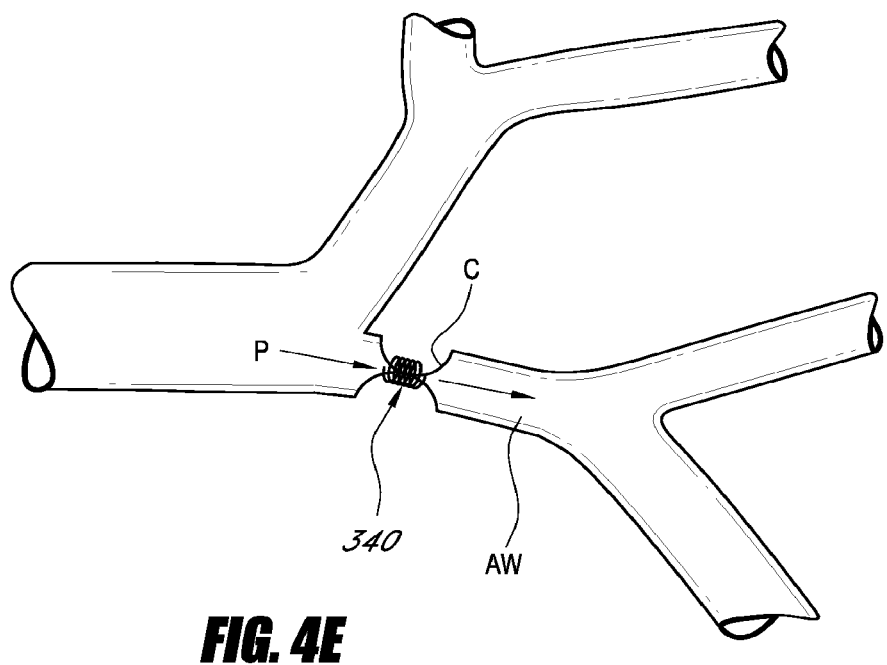

Referring to FIG. 4D, once closed the airway is closed, the airway closing device 300 may be withdrawn, leaving a closed airway and the suture 340 (or other closing implement, or in some embodiments no implement). The suture 340 has acted to close the airway and remains in the airway after the device 300 has been withdrawn. Once the airway has been sutured or stapled, the resulting airway restriction produces atelectasis over a period of time. Also, as shown in FIGS. 4D and 4E, the airway may either be completely closed (FIG. 4D) or partially closed (FIG. 4E) so that a narrow passage P is available for fluid exchange along the airway. When the airway is completely closed and that airway leads to a target lung compartment that is not subject to collateral ventilation, the closing will lead to a gradual collapse of the diseased lung portions distal to the closing point. The collapse occurs because the closing causes the air trapped in the compartment to diffuse out through the capillaries. In the case of partial closing, it is expected to lead to hypoxia in the portions of the lung fed by the airway, which would also lead to a gradual shrinkage of the diseased lung tissue therein. In both cases, the shrinkage or collapse of the diseased portions of the lung often improves the function of the healthier portions of the lung.

Optionally, the lung compartment that the airway feeds is collapsed by an additional collapsing mechanism prior to or contemporaneously with the closing of the airway. For example, after a lung compartment has been determined to exhibit collateral ventilation, a lung compartment collapsing mechanism may be used to evacuate and collapse the lung compartment distal to the point of intended airway closing. For example, a vacuum may be provided via a suction tube to evacuate and collapse the lung compartment. Thereafter, the airway closing mechanism 330, with or without a closing implement such as the suture 340, may be used to close the airway.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A device for selecting a size of a pulmonary implant to be implanted in an airway in a human or animal subject, the device comprising:
    a flexible catheter body having a proximal end, a distal end, and a longitudinal axis;
    a first fixed length flexible sizing element and a second fixed length flexible sizing element disposed along and extending approximately orthogonally relative to the longitudinal axis from the catheter body, wherein the first and second sizing elements have different heights from one another, and wherein the first and second sizing elements are configured to fit through the working channel of a bronchoscope;
    wherein the first fixed length flexible sizing element comprises two fixed length flexible tabs disposed approximately opposite one another across the longitudinal axis and extending approximately orthogonally relative to the longitudinal axis, and wherein the second fixed length flexible sizing element comprises two fixed length flexible tabs disposed approximately opposite one another across the longitudinal axis and extending approximately orthogonally relative to the longitudinal axis; wherein each orthogonally extending fixed length flexible tab has a single attachment to the catheter body;
    wherein the pulmonary implant is an expandable pulmonary implant, and wherein the first sizing element has a first height corresponding to a maximum diameter of the pulmonary implant in a deployed configuration, and the second sizing element has a second height corresponding to a minimum diameter of the pulmonary implant in the deployed configuration.

2. A device for selecting a size of a pulmonary implant to be implanted in an airway in a human or animal subject, the device comprising:
    a flexible catheter body having a proximal end, a distal end, and a longitudinal axis;
    a first fixed length flexible sizing element and a second fixed length flexible sizing element disposed along and extending approximately orthogonally relative to the longitudinal axis from the catheter body, wherein the first and second sizing elements have different heights from one another, and wherein the first and second sizing elements are configured to fit through the working channel of a bronchoscope;
    wherein the first fixed length flexible sizing element comprises two fixed length flexible tabs disposed approximately opposite one another across the longitudinal axis and extending approximately orthogonally relative to the longitudinal axis, and wherein the second fixed length flexible sizing element comprises two fixed length flexible tabs disposed approximately opposite one another across the longitudinal axis and extending approximately orthogonally relative to the longitudinal axis; wherein each orthogonally extending fixed length flexible tab has a single attachment to the catheter body;
    wherein the sizing elements are disposed proximally along the catheter body relative to the distal end, and wherein a distance between the distal end and the sizing elements corresponds to a length of the pulmonary implant.

3. A device for selecting a size of a pulmonary implant to be implanted in an airway in a human or animal subject, the device comprising:
    a flexible catheter body having a proximal end, a distal end, and a longitudinal axis;
    a first fixed length flexible sizing element and a second fixed length flexible sizing element disposed along and extending approximately orthogonally relative to the longitudinal axis from the catheter body, wherein the first and second sizing elements have different heights from one another, and wherein the first and second sizing elements are configured to fit through the working channel of a bronchoscope; and
    a depth marker disposed along the catheter body at a distance from the distal end corresponding approximately to a length of the pulmonary implant;
    wherein the first fixed length flexible sizing element comprises two fixed length flexible tabs disposed approximately opposite one another across the longitudinal axis and extending approximately orthogonally relative to the longitudinal axis, and wherein the second fixed length flexible sizing element comprises two fixed length flexible tabs disposed approximately opposite one another across the longitudinal axis and extending approximately orthogonally relative to the longitudinal axis; wherein each orthogonally extending fixed length flexible tab has a single attachment to the catheter body.

4. The method for selecting a size of a pulmonary implant to be implanted an airway in a human or animal subject, the method comprising:
   inserting a bronchoscope into the airway;
   advancing an elongate airway measuring device through a channel in the bronchoscope to expose within the airway a distal end of the measuring device and first and second fixed length flexible sizing elements disposed near the distal end and extending approximately orthogonally relative to a longitudinal axis of the measuring device, wherein the sizing elements have different heights from one another; wherein the first fixed length flexible sizing element comprises two fixed length flexible tabs disposed approximately opposite one another across the longitudinal axis and extending approximately orthogonally relative to the longitudinal axis, and wherein the second fixed length flexible sizing element comprises two fixed length flexible tabs disposed approximately opposite one another across the longitudinal axis and extending approximately orthogonally relative to the longitudinal axis; wherein each orthogonally extending fixed length flexible tab has a single attachment to an elongate body of the measuring device;
   observing, using the bronchoscope, the fixed length flexible sizing elements in relation to a wall forming the airway; and
   selecting the size of the pulmonary implant based on the observation of the sizing elements; wherein the selecting step comprises:
      selecting a smallest size of the pulmonary implant if both the first and second fixed length flexible sizing elements are touching the wall during the observing step;
      selecting an intermediate size of the pulmonary implant if the first fixed length flexible sizing element is not touching the wall and the second fixed length flexible element is touching the wall during the observing step; and
      selecting a largest size of the pulmonary implant if neither the first nor the second fixed length flexible sizing element is touching the wall during the observing step.

5. The method of claim 4, further comprising:
   observing that both the distal end and the sizing elements of the measuring device are located within the airway; and
   confirming, based on the observation of the distal end and sizing elements, that the airway is long enough for the pulmonary implant to be implanted therein.

6. A device for selecting a size of a pulmonary implant to be implanted in an airway in a human or animal subject, the device comprising:
   a flexible catheter body having a proximal end, a distal end, and a longitudinal axis;
   a first fixed length flexible sizing element and a second fixed length flexible sizing element disposed along and extending approximately orthogonally relative to the longitudinal axis from the catheter body, wherein the first and second sizing elements have different heights from one another, and wherein the first and second sizing elements are configured to fit through the working channel of a bronchoscope;
   wherein the first fixed length flexible sizing element comprises two fixed length flexible tabs disposed approximately opposite one another across the longitudinal axis and extending approximately orthogonally relative to the longitudinal axis, and wherein the second fixed length flexible sizing element comprises two fixed length flexible tabs disposed approximately opposite one another across the longitudinal axis and extending approximately orthogonally relative to the longitudinal axis; wherein each orthogonally extending fixed length flexible tab has a single attachment to the catheter body;
   wherein the first sizing element has a first height corresponding to a maximum diameter of the of the airway in which the pulmonary implant may be functionally delivered, and the second sizing element has a second height corresponding to a minimum diameter of the airway in which the pulmonary implant may be functionally delivered.

7. A device for selecting a size of a pulmonary implant to be implanted in an airway in a human or animal subject, the device comprising:
   a flexible catheter body having a proximal end, a distal end, and a longitudinal axis;
   a first fixed length flexible sizing element and a second fixed length flexible sizing element disposed along and extending approximately orthogonally relative to the longitudinal axis from the catheter body, wherein the first and second sizing elements have different heights from one another, and wherein the first and second sizing elements are configured to fit through the working channel of a bronchoscope;
   wherein the first fixed length flexible sizing element comprises two fixed length flexible tabs disposed approximately opposite one another across the longitudinal axis and extending approximately orthogonally relative to the longitudinal axis, and wherein the second fixed length flexible sizing element comprises two fixed length flexible tabs disposed approximately opposite one another across the longitudinal axis and extending approximately orthogonally relative to the longitudinal axis; wherein each orthogonally extending fixed length flexible tab has a single attachment to the catheter body;
   wherein the sizing elements are disposed proximally along the catheter body relative to the distal end, and wherein a distance between the distal end and the sizing elements corresponds to a minimum length of the airway in which the pulmonary implant may be functionally delivered.

8. A device for selecting a size of a pulmonary implant to be implanted in an airway in a human or animal subject, the device comprising:
   a flexible catheter body having a proximal end, a distal end, and a longitudinal axis;
   a first fixed length flexible sizing element and a second fixed length flexible sizing element disposed along and extending approximately orthogonally relative to the longitudinal axis from the catheter body, wherein the first and second sizing elements have different heights from one another, and wherein the first and second sizing elements are configured to fit through the working channel of a bronchoscope; and a depth marker disposed along the catheter body at a distance from the distal end corresponding approximately to a minimum length of the airway in which the pulmonary implant may be functionally delivered;

wherein the first fixed length flexible sizing element comprises two fixed length flexible tabs disposed approximately opposite one another across the longitudinal axis and extending approximately orthogonally relative to the longitudinal axis, and wherein the second fixed length flexible sizing element comprises two fixed length flexible tabs disposed approximately opposite one another across the longitudinal axis and extending approximately orthogonally relative to the longitudinal axis; wherein each orthogonally extending fixed length flexible tab has a single attachment to the catheter body.

\* \* \* \* \*